United States Patent [19]

Stevens

[11] Patent Number: 5,738,742
[45] Date of Patent: Apr. 14, 1998

[54] METHOD FOR MAKING ANGIOGRAPHIC CATHETERS

[76] Inventor: Robert C. Stevens, 18265 NW. Highway 335, Williston, Fla. 32696

[21] Appl. No.: 747,360

[22] Filed: Nov. 12, 1996

[51] Int. Cl.⁶ .................... A61M 25/00; B32B 1/10
[52] U.S. Cl. .................... 156/149; 156/154; 156/244.12; 156/244.14
[58] Field of Search .................... 156/149, 154, 156/155, 244.12, 244.14; 264/103, 171.27; 604/282

[56] References Cited

U.S. PATENT DOCUMENTS

| | | | |
|---|---|---|---|
| 3,485,234 | 12/1969 | Stevens | 604/282 |
| 3,585,707 | 6/1971 | Stevens | 264/103 |
| 4,904,431 | 2/1990 | O'Maleki | 156/149 |
| 5,514,236 | 5/1996 | Avellanet | 156/149 |
| 5,560,103 | 10/1996 | Harris | 156/154 |

Primary Examiner—Daniel Stemmer
Attorney, Agent, or Firm—Fay, Sharpe, Beall, Fagan, Minnich & McKee

[57] ABSTRACT

A method of manufacturing angiographic catheters comprises providing a length of elastomeric tube of a predetermined outer diameter and braiding multiple strands of wire wrapping about its exterior. A bonding agent is applied to the wire wrapping in circumferentially extending bands to bond the strands to each other. Thereafter, the wire wrapping is ground away at predetermined spaced locations along the length of the elastomeric tube to provide a series of wire wrapped sections joined by non-wrapped sections with each of the wire wrapped sections having at least the ends thereof enclosed by at least portions of the circumferentially extending bands of bonding agent. An elastomer layer is located over both the wire wrapped sections and the non-wrapped sections throughout the length thereof. Subsequently, the coated length is severed into pieces with the pieces each constituting a wire wrapped section that forms a catheter body and a non-wrapped section joined to at least one end thereof to constitute a flexible catheter tip.

8 Claims, 4 Drawing Sheets

METHOD FOR MAKING ANGIOGRAPHIC CATHETERS

BACKGROUND OF THE INVENTION

The subject invention is directed toward the art of angiographic catheters and, more particularly, to an improved method for manufacturing such catheters.

Angiographic catheters are used for diagnostic purposes as well as for angioplasty. It is generally agreed that a good catheter should have the following features:

a) torsion control with a 1:1 rotation about its central longitudinal axis even when subjected to curvatures of as much as 110° along the catheter's length;

b) the ability to withstand high injection pressures of as much as 1000 PSI which are required where large amounts of contrast media is needed to properly visualize a given area to be studied;

c) push ability in conjunction with good torsional control along its axis mandates a catheter body having a controlled rigidity since if too rigid, it can cause injury and if too flexible, it may buckle;

d) a controlled degree of flexibility at the catheter tip is necessary to prevent injury to vessel openings and to vessel walls and this can be accomplished by using a softer plastic in this region, annular grooving, or decreasing the diameter as compared to the catheter body; and, e) the catheter tip must be easily formed and must retain the formed shape even when subjected to straightening when passed over a guide wire.

A catheter with the above features is described in my prior U.S. Pat. No. 3,485,234, which issued Dec. 23, 1969. My prior U.S. Pat. No. 3,585,707, which issued Jun. 22, 1971, sets forth how to make or manufacture the catheter.

The catheter construction described in these prior patents uses a wire braid reinforcing to provide torsional control and to withstand high pressure injections. In order to have a flexible tip with good shape memory, it is necessary that no wire braid be in the tip area. The earlier patents describe the manner in which a tip portion is added to the catheter body. The tip portion, without braid, is formed as a separate item and is molded or fused to the end of the catheter body. This has been the weakest portion of the catheter, since the tip may become loosened or separated over a period of time or from physical abuse such as using an oversized guide wire, severe twisting or attempts at re-shaping the curvature of the tip.

Another problem with the original construction of this catheter is that it has been necessary to mold or fuse the tip by hand. This is very labor intensive and, therefore, expensive. In this age of rising medical costs, it is even more important than ever to reduce manufacturing costs.

I have now devised a method to eliminate the molding or fusing of the tip to thereby allow the catheter to be made as a single, unitary unit. All of the good features of the original catheter construction have been preserved including the wire braid in the body of the catheter and no braid in the tip area. The method can be fully automated, eliminating the hand crafting of the catheter tip. This can make the catheter safer and less expensive to manufacture.

The subject inventive method and its advantages can best be appreciated by first understanding the manufacturing process used for the original catheters. The original process is generally set forth in the flow chart of FIG. 1. In particular, the process involves the following steps (the paragraph numbers correspond to the sequence number shown in FIG. 1):

1) The process starts by forming a length of elastomeric tube. The tube is formed by starting with a silver plated copper wire or a monofilament of plastic (such as "Celcon" manufactured by the Hoechst Celanese Corporation, or Ultraform, an acetal copolymer manufactured by BASF), of a diameter equal to the published lumen diameter of the catheter being manufactured. This wire or monofilament is referred to as the "mandrel." As an example, a standard French 7 catheter has a lumen of 0.046 inches and an outside diameter of 0.092 inch. The wire or monofilament is purchased and used in continuous lengths of over 5000 feet. This wire or monofilament is referred to as a "mandrel" because the catheter is built on it.

The mandrel is passed through a plastic extruder, coating the mandrel with the selected elastomer to approximately 0.006 inch wall thickness. The elastomer or plastic used, for example, could be polyurethane containing bismuth or barium to make it opaque to x-rays, or radiopaque.

2) The coated mandrel is then placed in a "braiding machine" which overlays the elastomeric tube extrusion with multiple (e.g., 16) strands of 0.003 inch or smaller diameter stainless steel wire.

3) After the entire length of elastomeric extrusion has been overlaid with the wire braid, it is then cleaned in an ultrasonic cleaning bath and again passed through the plastic extruder adding another layer of plastic creating a wall thickness of approximately 0.012 inch. The combined layers of plastic and wire braid on the 0.046 inch diameter mandrel will now be approximately 0.094 inch in diameter.

4) Catheter tip material requires only a single extrusion on a corresponding mandrel wire because no braiding is required. The single layer of plastic applied to a 0.046 inch mandrel will have a wall thickness of 0.024 inch for a total diameter of 0.094 inch.

5) The body material and the tip material is cut to lengths of approximately 42 inches. This mandrel is now removed from within the cut lengths of body and tip material. This is done by stretching the mandrel, if necessary, to reduce its diameter and facilitate its withdrawal from within the plastic extrusion.

6) This material is then passed through a centerless grinder and ground to the proper diameter size and to a fine, smooth surface.

7) The tip material is then cut to lengths of approximately 3½ inches and tapers are ground on one end where necessary and a flare is formed at the other end.

8) The body material is ground to a taper at one end to mate with the internal taper of the flared tip portion.

9) A steel rod approximately 0.044 inch diameter is inserted into a catheter body and a tip is slipped onto the rod and the external taper of the body is mated with the internal taper of the tip.

10) Next, a sleeve or tube of Teflon about 6 inches in length is passed over the tip-body mated section. The tip-body with the Teflon sleeve are then pressed through a die that has been heated to approximately 325° F. The heat plus the pressure of the sleeve fuses and mold the joined sections by melting the plastic of both parts into a smooth joint. Where necessary, the catheter assembly is again passed through the centerless grinder, particularly if the fused joint is slightly larger than the rest of the catheter. It is important that the catheter with tip be within ±0.001 inch of the published diameter.

11) The finished catheter is cut to the published length, a luer hub is added to the proximal end and the tip portion is

3 then shaped with a forming wire in boiling water. The shapes of catheter tips are many, such as a single curve, double curve, Judkins left, Judkins right, pigtail, etc.

SUMMARY OF THE INVENTION

The subject invention greatly simplifies the process of forming the catheters by eliminating several of the above-described steps. In addition, the process is not only simplified, but also results in a significantly better product. In particular, and in accordance with the subject invention, the method of manufacturing angiographic catheters generally comprises forming a length of cylindrical elastomeric tube of a predetermined outer diameter and braiding multiple strands of wire wrapping about the elastomeric tube. Thereafter, a bonding agent is applied to the wire wrapping circumferentially thereof at spaced locations to cause the strands of wire wrapping to be bonded to each other and to the elastomer. Subsequent to the bonding, predetermined sections of the wire wrapping are removed from the elastomeric tube to leave the length of elastomeric tube with multiple wire wrapped sections spaced from one another by unwrapped sections such that each wire wrapped section has axially spaced ends enclosed by the bonding agent to prevent loosening or unwinding of the wire wrapping. Over the length of the elastomeric tube with the multiple wire wrapped sections, there is coated a continuous layer of elastomer to produce a uniform diameter length of elastomeric coated wire wrapped sections spaced from one another by unwrapped sections. The continuous length thus produced is thereafter cut transversely at locations selected to reduce the length to multiple pieces of coated wire wrapped sections each having a coated unwrapped section joined thereto at least one end thereof. The wire wrapped section of this length forms the main length and body of the catheter while the unwrapped section forms a continuous integral tip for the catheter. The tip section can, of course, be further treated to taper it and/or shape it to a desired shape. The method thus forms the main body of the catheter and the tip as a unitary structure eliminating the previously-required separate formation of the two elements following by the labor-intensive forming and bonding necessary in the prior art process.

It is also contemplated that the coating of the continuous layer of elastomer over the length of elastomeric tube with the multiple wire wrapped sections will be accomplished by a conventional extruding operation.

It should be appreciated that there may be variations of the basic inventive process. The actual length in which the components are produced can also vary widely. Similarly, the orientation of the individual sections that are subsequently cut into separate and individual catheters can, of course, be varied and the types of elastomers used at various times during the process can differ.

As can be seen from the foregoing, a primary object of the invention is the provision of a simplified process for forming angiographic catheters.

A still further object of the invention is the provision of a method of the general type described wherein the main body of the catheter and its associated tip are formed integrally to eliminate numerous bonding and finishing steps required by the prior art processes.

Yet another object of the invention is the provision of a process of the type described wherein the processing can be accomplished with conventional well known types of grinding, braiding, and extruding machinery.

Still other advantages and benefits of the invention will become apparent to those skilled in the art upon a reading and understanding of the following detailed description.

4

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein.

DETAILED DESCRIPTION OF THE PREFERRED EMBODIMENT

Figure 1:
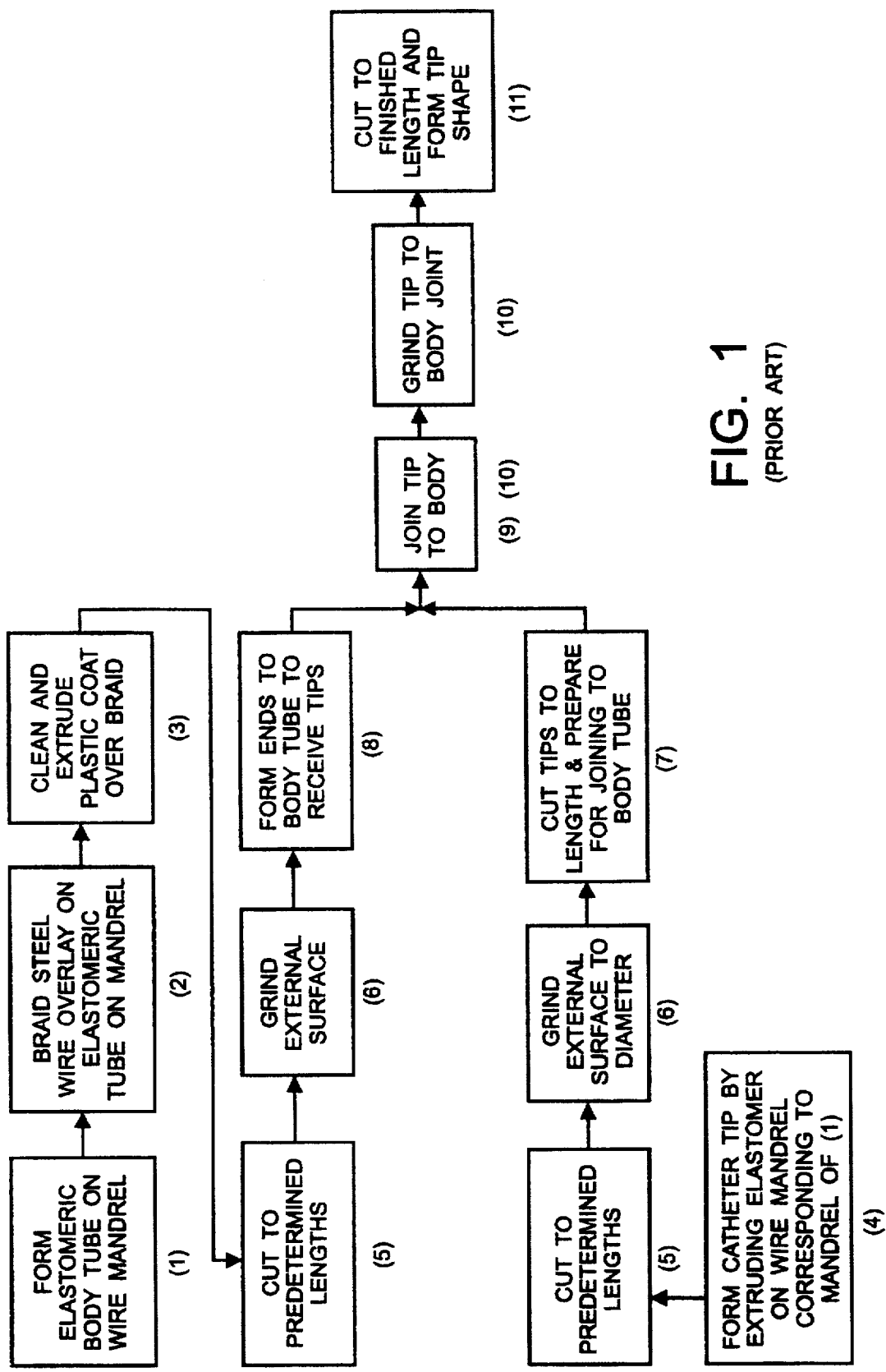
FIG. 1 is a flow chart showing a typical prior art processing method used for forming angiographic catheters.
Figure 2:
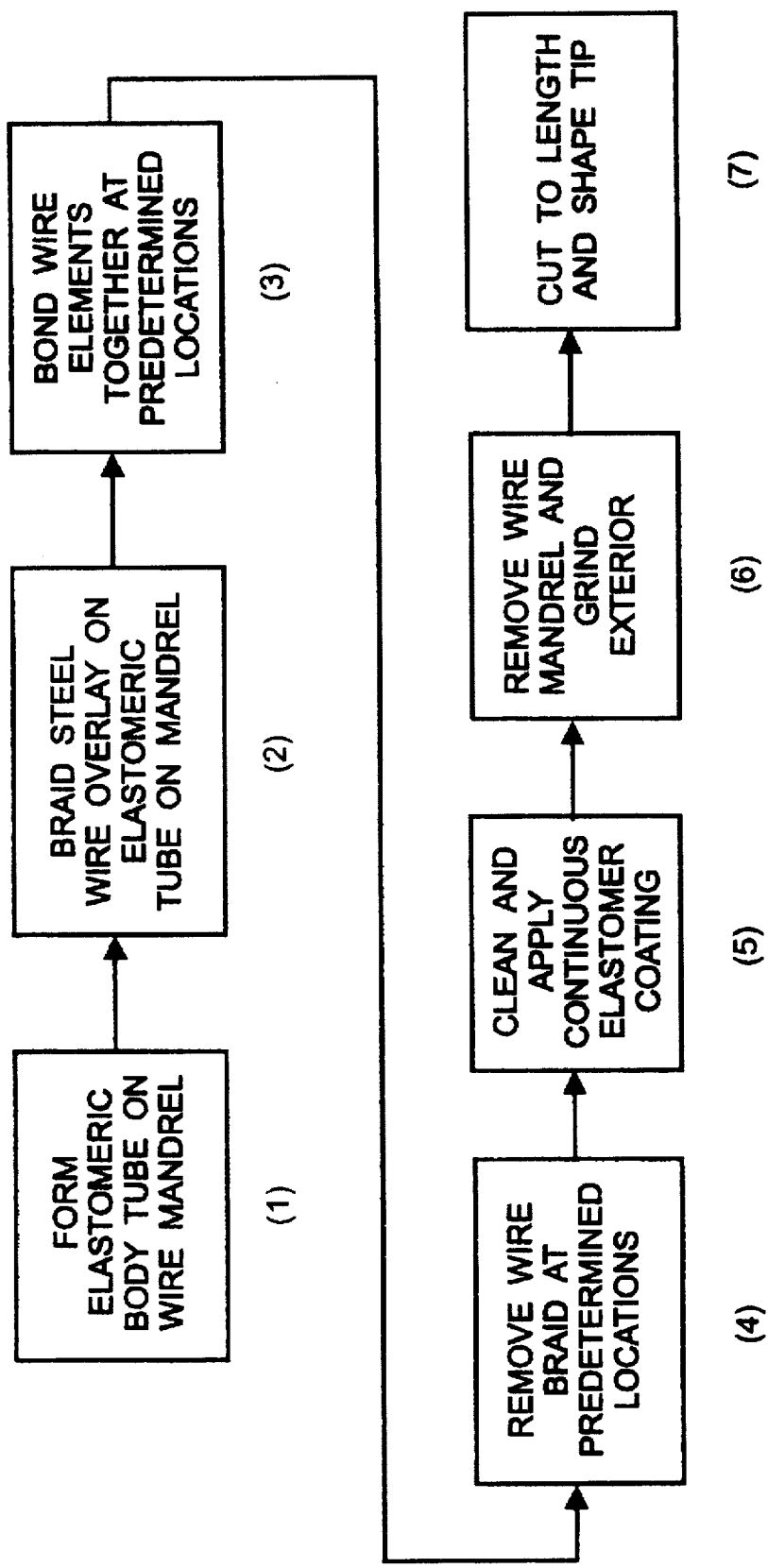
FIG. 2 is a process chart similar to FIG. 1 but showing the preferred processing steps according to the invention.

Referring now to the drawings wherein the showings are for the purposes of illustrating the preferred embodiment of the invention only and not for purposes of limiting same, in FIG. 2, the full sequence of steps for the preferred embodiment of the inventive process are set forth in relative diagrammatic form. It will be noted in comparing FIG. 2 to the prior art process shown in FIG. 1 and previously described that there is no separate sequence of steps required to form tip sections. Rather, the entire sequence of steps involves a progressive processing of what is basically a single element. In particular, as shown in FIG. 2, the process begins by the formation of an elastomeric tube that has an internal open diameter that corresponds to the desired internal diameter equal to the lumen diameter of the catheter to be made. The elastomeric body tube could be formed in other ways, but in the preferred form of the invention, it is formed by extruding a desired elastomeric material such as a relatively soft polyurethane onto a plated copper wire or monofilament of a suitable plastic having the desired lumen diameter. The wire can be in substantially any desired length, but is preferably a substantial number of multiples of the desired final length of the catheter being formed. The wire or monofilament which is to function as the mandrel in the formation of the basic elastomeric body tube is passed through a conventional extruder to coat the mandrel with a selected thickness of elastomer which would vary depending upon the size of the catheter being made. Thereafter, the elastomeric tube with the mandrel in place is passed through a conventional braiding machine which overlies the elastomeric body tube with multiple strands of a small diameter stainless steel wire. For example, it is common to use 16 strands of 0.003 inch diameter wire which is braided onto the elastomeric body tube in the manner discussed in my prior U.S. Pat. No. 3,585,707 which is incorporated herein by reference.

Thereafter, the braided overlay is coated at predetermined selected locations with a suitable coating capable of bonding the wire elements in the braided body together. Epoxy coatings have been used for this purpose. Coatings that can be UV cured are preferred because they can be cured in seconds. The coating over the braided sections can be applied with rollers, brushed on, or sprayed. It is important that only enough epoxy or other adhesives be applied to fill the interstices of the wire braid and onto the base coating. In the preferred form, when making a catheter having a length of 42 inches, the epoxy coating is applied to a width of approximately 4½ inches every 42 inches. As will become apparent from the following description, alternatives to this are possible. For example, it would be possible to apply epoxy coating for 1 inch leaving a 2½ inch uncoated section followed by a further 1 inch coating of epoxy. The reasons for this and the alternatives thereto will become apparent from the further description of the process.

Subsequent to the epoxy coating in the manner described above, the length of braided and epoxy coated stock is treated so as to remove approximately 3½ inches of braided material every 42 inches within the epoxy coated section to leave approximately ¾ inch of epoxy coated material on either side of the portion that has had the braid removed. The epoxy holds the remaining braided sections in place and prevents unraveling. Preferably, and in accordance with the preferred embodiment, the braid is removed by a grinding operation. The depth of the grind is approximately 0.006 inch so that the braiding is removed down to the base coat which is the formed elastomeric tube formed in the first step.

Centerless grinders are widely used in industry and in angiographic catheter manufacture in particular. Catheter stock is "fed" though the grinder to remove excess plastic and to bring it to an accurate diameter. The grinder also creates a smooth surface finish. Centerless grinders are also used to grind tapers on catheter tips.

In centerless grinding, the machine weighs over 1000 pounds. This helps to give it great accuracy (±0.0001 inch). The grinding wheel used in catheter production can be 6-8 inches in diameter with a width of 4 inches or greater. Perfect balancing is mandatory.

In centerless grinding, the part to be ground must be rotated under the grinding wheel. This is not a problem where the part is inches or even a few feet in length. However, where the part to be ground is 5000 feet or longer, this is not very satisfactory. With 5000 feet of braided catheter material on a spool weighing 50 pounds or more, it is not generally practical to rotate the spool at speeds of at least 200 RPM. Not only would you have to rotate the spool, but also feed off sections of braided material every 42 inches as you rotate.

In order to rotate the catheter stock during grinding and use the standard heavy but accurate centerless grinders currently available, I have devised a means to rotate only the portion of the catheter stock to be ground.

Figure 3:
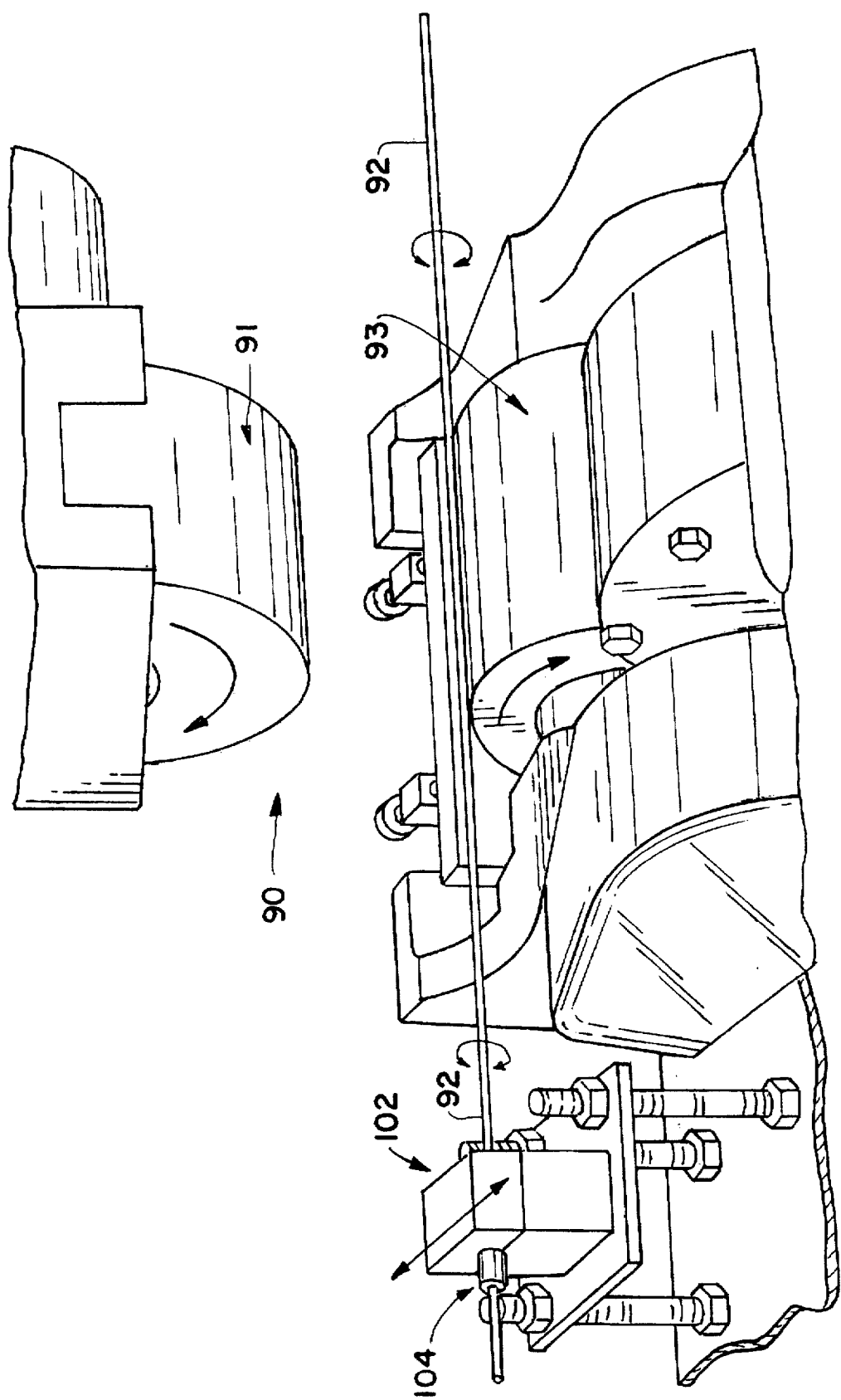
FIG. 3 is a somewhat diagrammatic view of grinding apparatus used for removing predetermined lengths of wire wrapping from the length of elastomeric tube; and, FIG. 4 is a pictorial view of the apparatus used for rotating the wire wrapped tube while the wrapping removal step is performed.
Figure 4:
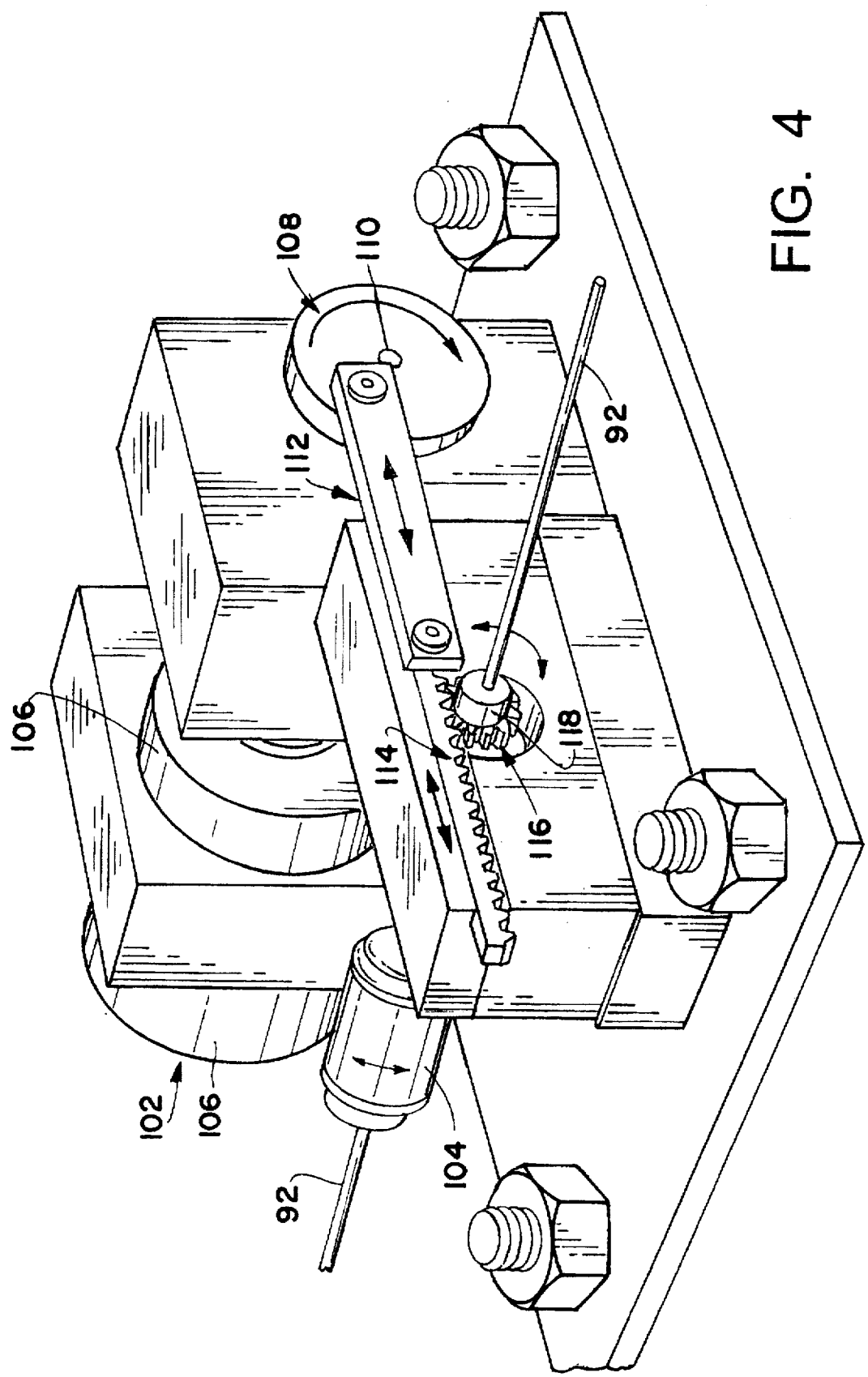

Referring in particular to FIGS. 3 and 4, my preferred form of grinding apparatus can be understood. Specifically, the grinder 90 is a centerless grinder modified by the addition of a motor driven clamping device 102 having a releasable collet 104 which firmly grips the wire braided stock just aft of the epoxy coated section and rotates, for example, 360° clockwise, then 360° counterclockwise to expose the entire circumference of the wire braided area to be removed by the grinder. The grinder 90 includes an upper grinding wheel 91 and a support wheel 93 arranged to engage on opposite sides of the catheter stock 92 passing therebetween. The operation and control of the grinder is well known.

The device 102 (see FIG. 4) is driven by motor 106 with a crank arm 108 attached to the motors output shaft 110. The crank arm 108 is connected with a connecting rod 112 that drives a rack gear 114 which rotates a pinion 116. The catheter stock passes through the center of the pinion 116. The pinion is attached to a rotatably mounted shaft 118 that supports collet 104, which firmly grips the braided stock just aft of the epoxy coated section. As the rack gear 114 moves back and forth, a reciprocating back and forth motion of the collet is generated. A rate of about 200 RPM for shaft 118 has been found satisfactory.

After the braid has been removed in the desired areas, the braided and non-braided continuous section of stock is run through a plastic extruder and the finished coat of elastomer applied to a uniform diameter throughout the entire length of base stock resulting in the alternate sections of braid reinforced and non-braided sections. Subsequently, the wire mandrel is removed. Thereafter, the entire length of catheter material is ground to have the desired final exterior catheter diameter with a proper surface smoothness. This is a known form of grinding using a centerless grinder. The catheter sections are cut to length which results in a main wire reinforced body and a 3½ inches non-reinforced tip portion. The tip portion can be subsequently tapered and/or shaped as desired. Additionally, thereafter, hub or other elements are added to the catheter body, as needed.

As can be seen, the described method can be varied widely. It is important to note, however, that the labor-intensive problems involved with attaching a separate tip to a wire braid reinforced catheter body are totally eliminated by the subject processing. Additionally, grinding the joint between the tip and the body is eliminated. This elimination of the added steps and labor results in a less expensive catheter construction. In addition to reduced labor costs, the resulting catheter is significantly better because the possibility of failure at a bonded section are totally eliminated.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. A method of manufacturing angiographic catheters comprising:
   a) forming a length of cylindrical elastomeric tube of a predetermined outer diameter;
   b) braiding multiple strands of wire wrapping about the said elastomeric tube;
   c) applying to the wire wrapping circumferentially extending bands of a bonding agent at spaced locations to bond the strands of wire wrapping to each other and the elastomeric tube;
   d) removing predetermined sections of the wire wrapping from about the elastomeric tube to leave the length of elastomeric tube with multiple wire wrapped sections spaced from one another by unwrapped sections, each wire wrapped section having axially spaced ends enclosed by bonding agent applied in step (c);
   e) coating a continuous outer layer of elastomer over the length of elastomeric tube with multiple wire wrapped sections spaced from one another by unwrapped sections; and,
   f) thereafter, taking the coated length of elastomeric tube with multiple wire wrapped sections spaced from one another by unwrapped sections and cutting it transversely at locations selected to reduce said length to multiple pieces of coated wire wrapped sections each having a coated unwrapped section joined thereto at least one end thereof.

2. The method as set forth in claim 1 wherein the wire wrapping removed in step (d) is removed by grinding.

3. The method as set forth in claim 1 wherein the step of coating of step (e) is applied by extruding.

4. The method as set forth in claim 1 wherein the length of cylindrical elastomeric tube formed in step (a) is formed by extruding elastomer over a wire or plastic mandrel.

5. The method as set forth in claim 4 including the step of removing the mandrel from the cylindrical elastomeric tube.

6. A method of manufacturing angiographic catheters comprising:
  a) providing a length of elastomeric tube of a predetermined outer diameter and braiding multiple strands of wire wrapper thereabout;
  b) applying a bonding agent to the wire wrapping in circumferentially extending bands to bond the strands of wire wrapping to each other;
  c) grinding away the wire wrapping at predetermined spaced locations along the length of the elastomeric tube to provide a series of wire wrapped sections joined by non-wrapped sections with each of the wire wrapped sections having at least one end thereof enclosed by portions of the said circumferentially extending bands of bonding agent;
  d) coating an elastomer over both the wire wrapped sections and the non-wrapped sections throughout the length thereof; and,
  e) thereafter, severing the coated length into pieces with the pieces each constituting a wire wrapped section with a non-wrapped section joined to at least one end thereof.

7. The method as set forth in claim 6 wherein the bonding agent applied to the wire wrapping in step (b) is applied in bands having an axial length greater than the axial length of the non-wrapped section resulting from step (c).

8. The method as set forth in claim 7 wherein the non-wrapped sections produced by the grinding of step (a) are produced centrally of the bands of bonding agent.

* * * * *